United States Patent [19]

Curcio

[11] Patent Number: 5,718,236
[45] Date of Patent: Feb. 17, 1998

[54] ERGONOMIC CONDOM

[76] Inventor: John A. Curcio, 101 Shale St., Staten Island, N.Y. 10314

[21] Appl. No.: 542,956

[22] Filed: Oct. 13, 1995

[51] Int. Cl.$^6$ ................................................. A61F 6/04
[52] U.S. Cl. ............................................ 128/844; 128/918
[58] Field of Search ............................. 128/842, 844, 128/918; 604/347–353

[56] References Cited

U.S. PATENT DOCUMENTS 5,111,831  5/1992  Foggia .................................. 128/844
5,314,447  5/1994  Papurt .................................. 128/844
5,370,130  12/1994  Hoss .................................... 128/844

FOREIGN PATENT DOCUMENTS 0211350  6/1909  Germany .............................. 604/349

*Primary Examiner*—Michael A. Brown

[57] ABSTRACT

An elastomeric condom that covers the entire male genitalia. An elastomeric scrotal pouch is integrally molded with an elastomeric closed end tubular member. The tubular portion and the pouch are joined at a constriction band that runs at an oblique angle instead of being transverse to the axis of the tubular portion.

6 Claims, 2 Drawing Sheets

ERGONOMIC CONDOM

BACKGROUND OF THE INVENTION

The use of condoms as a means of preventing the incidence and spread of sexually transmitted diseases (STD) has increased significantly in recent years. This is particularly important in view of the appearance of antibiotic-resistant strains of pathogenic organisms responsible for diseases such as syphilis and gonorrhea, and especially in view of the incidence of acquired immunodeficiency syndrome (AIDS), for which there is still no cure.

Disclosures by the U.S. Centers for Disease Control and reports at the International AIDS Conferences have focused international attention on the proliferation of AIDS in the general population. The diseases with which AIDS has been or is suspected to be linked include Pneumocystitis carinii pneumonia, Kaposi's sarcoma, esophageal or bronchopulmonary candidiasis, extrapulmonary cryptococcus, cytomegalovirus internal organ infection, disseminated Mycobacterium avium complex or M. kansasii infection, chronic herpes simplex ulceration, chronic cryptosporidiosis enteritis, toxoplasmosis of the brain, high-grade B-cell non-Hodgkin's lymphoma, disseminated histoplasmosis, chronic isosporiasis enteritis, and lymphoid interstitial pneumonia in children.

Since condoms afford a safe, low cost and generally reliable means of containing the spread of STD's, the demand for condoms is increasing both in developed and developing countries. A major drawback of standard sheath-like condoms is their inability to provide an impermeable barrier for areas of the skin other than the shaft of the penis that come into contact during sexual intercourse. In particular, conventional condoms do not protect the skin of the scrotum. The art discloses several condoms that also enclose the scrotum. Protecting the scrotum with a condom poses difficult problems of comfort and reliability. It is inherently difficult to pull on a condom over the scrotum and also difficult to keep the condom snugly on the scrotum during sexual intercourse without causing the user needless discomfort or even pain. A common shortcoming of the scrotal protection condoms of the prior art is that the scrotal protection pouch is coaxial with the rest of the condom, meaning that the area of the condom material that is superior of the scrotal protection pouch bunches up after the condom is pulled on by the user. See, in particular, U.S. Pat. No. 5,318,042, issued Jun. 7, 1994. The disclosure of that patent suggests that the bunching up that is experienced after pulling on that condom will provide increased pleasure for the female partner during intercourse, but that statement appears dubious at best. Other condom designs have included a constricted band portion close to the comdoms's distal end (generally, the open end) that helps keep the condom on snugly in place during use. The designs of the prior art show such constricted bands at a perpendicular or transverse angle relative to the axis of the tubular portion of the condom. Use of such a constriction band with a scrotal protection condom would only exacerbate the bunching up problem described above.

It is an object of the present invention to provide a condom that provides added protection for the scrotum of the wearer from sexually transmitted diseases, and is constructed ergonomically to more closely approximate the true shape of the external male genitalia during sexual activity. It is another object of the present invention to provide such a condom that does not bunch up in the area superior of the scrotal pouch. It is another object of the present invention to provide for an additional constriction band to help ensure a snug effective fit of the condom during use. These and other objects of the invention will become clearer by reference to the following written description and accompanying illustrations.

SUMMARY OF THE INVENTION

In brief summary, the invention is an elastomeric condom, comprising a closed distal end portion to cover the glans of the penis; a non-axial hollow tubular portion to cover the shaft of the penis, integrally continuous from the closed distal portion, having an inner surface and an outer surface, and having an open proximal end, a scrotal pouch to cover the scrotum that is non-axial with the tubular portion, integrally continuous with the hollow tubular portion by an annular constricted band portion that is of lesser diameter than the tubular portion, the constricted band portion joining the tubular portion to the scrotal pouch at a non-perpendicular angle relative to the median axis of the tubular portion; and a formed constricted band portion that terminates the scrotal pouch and that is non-axial with the tubular portion, the band being of lesser diameter than the scrotal pouch. The annular constricted band that joins the tubular portion to the scrotal pouch comprises a ring of constricted elastomeric material that, when the condom is in place on the male genitalia, circumferentially covers the area that the scrotum is joined to the underside of the penis, the lateral areas that the scrotum is joined to the penis, and the area that the abdominal wall superiorly joins the penis.

DETAILED DESCRIPTION OF THE PREFERRED EMBODIMENTS AND BEST MODE OF THE INVENTION

Figure 1:
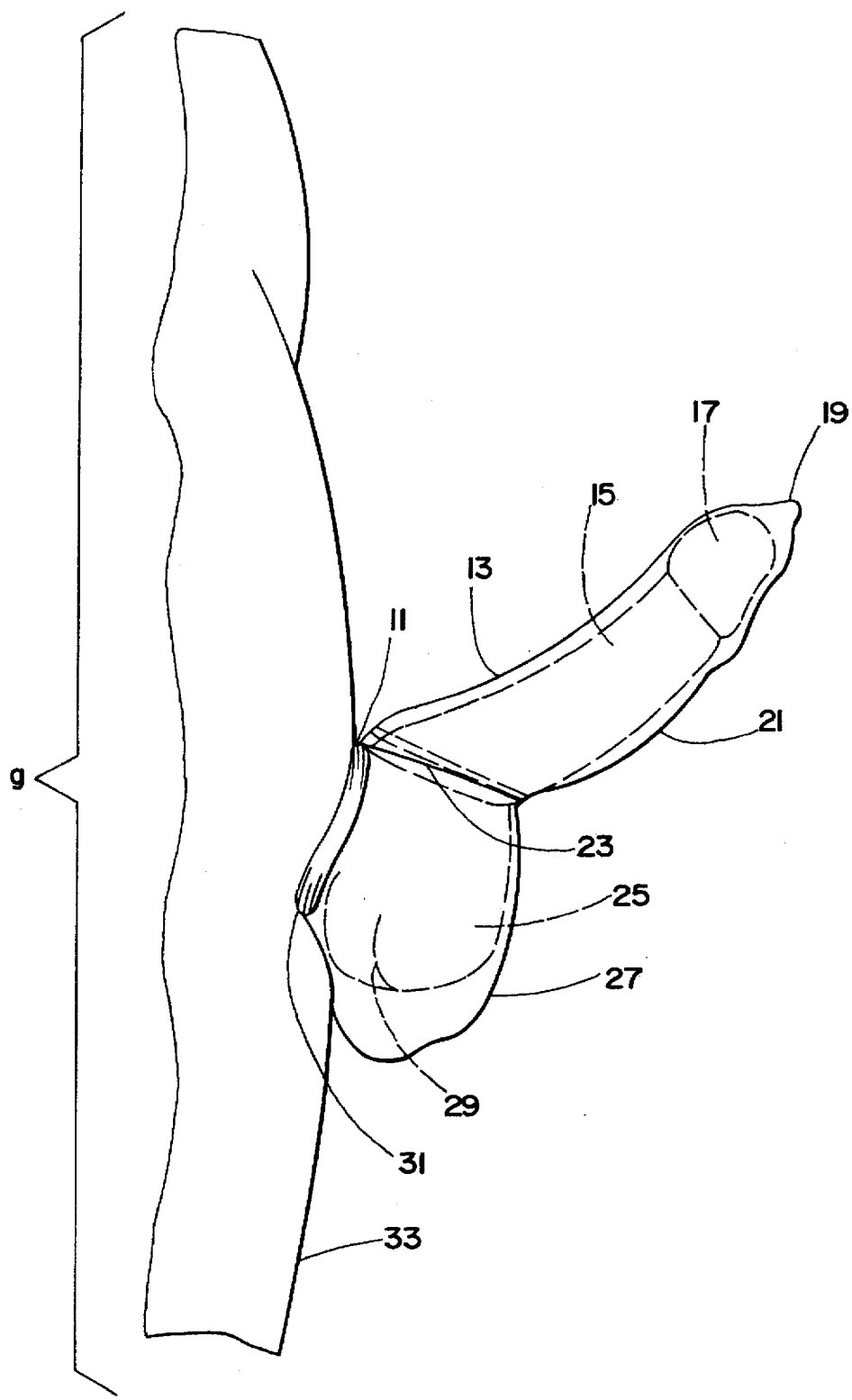
FIG. 1 is a side view of the condom of the invention, showing the condom placed over the male external genitalia.

Referring first to FIG. 1, there is seen in side view the condom of the invention in use by a wearer. Condom 13 is fitted over the male external genitalia, shown comprising the glans 17, the penis shaft 15, and the scrotum 25, also shown superficially bisected by raphae 29. Condom 13 has several constituent structural components. In a preferred embodiment of the invention, at the proximal end covering glans 17 is a teat 19 that is designed to collect and contain ejaculated semen to prevent its transmission to a partner during intercourse. The teat 19 is continuously and integrally an extension of the tubular portion of condom 13. The volume of teat 19 should be approximately in the range of from 3 to 10 cubic centimeters.

In an alternative embodiment of the invention, covering the inferior surface of the penis, there is an elongated hollow cavity 21 that is designed to more closely conform to the shape of the erect penis. The penis is attached to the front and sides of the pubic arch. In the flaccid condition it is cylindrical in shape, but when erect assumes the form of a triangular prism with rounded angles, one side of the prism forming the dorsum. It is composed of three cylindrical masses of cavernous tissue bound together by fibrous tissue and covered with skin. Two of the masses are lateral, and are known as the corpora cavernosa penis. The third is median, and is termed the corpus spongiosum penis, which contains the greater part of the urethra. The cavity 21 accounts for the contour formed by the corpus spongiosum during sexual activity, and thus adds better fit and more comfort.

Figure 2:
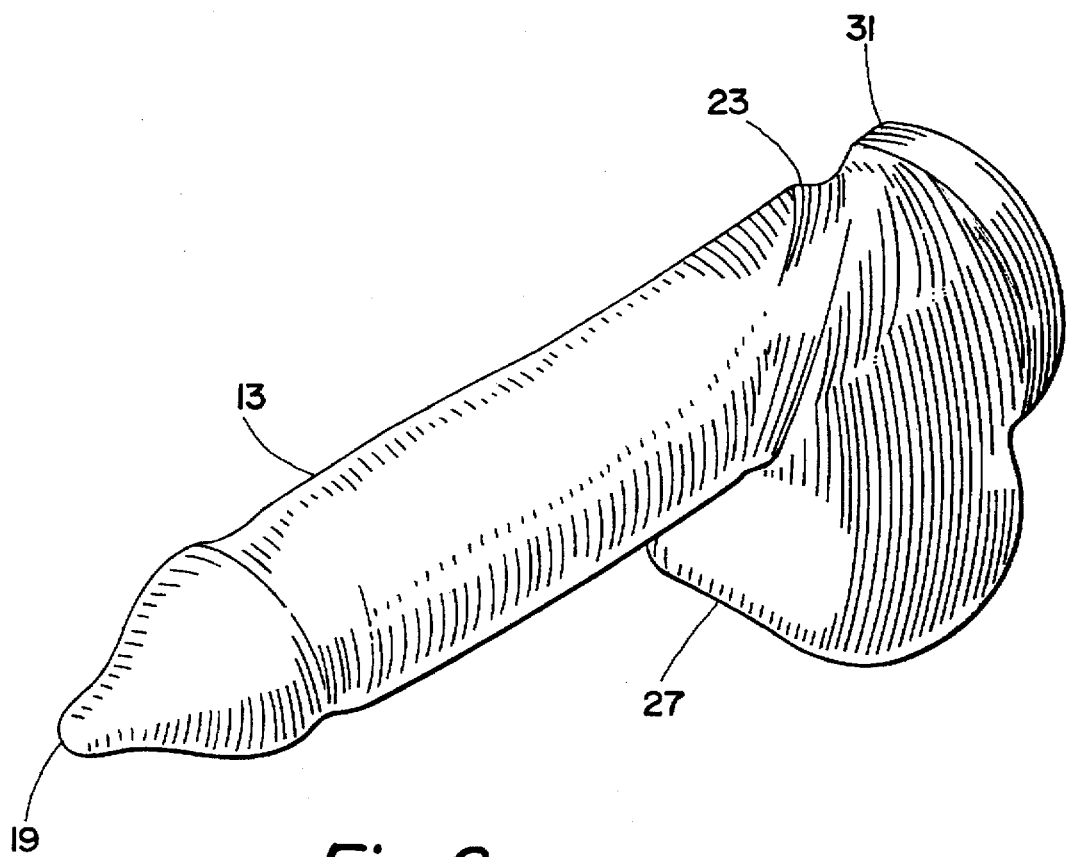
FIG. 2 is a perspective view of the condom of the invention.
Figure 3:
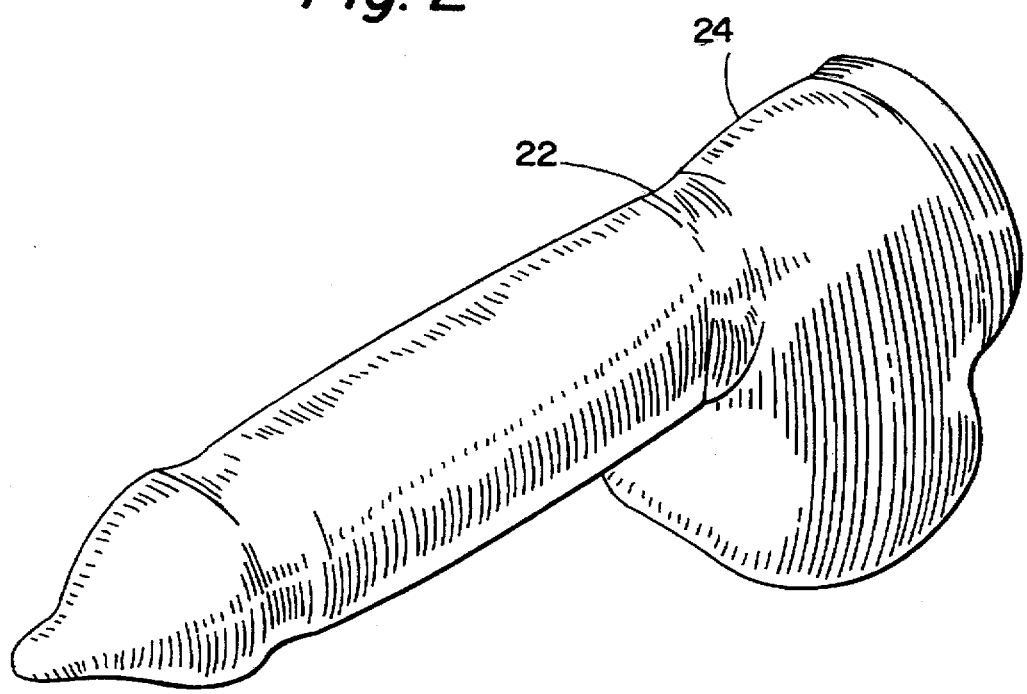
FIG. 3 is a perspective view of the prior art, showing the prior art placement of the constriction band transverse to the axis of the tubular portion of the condom.

In the most preferred embodiment of the invention, a constricted band 23 is formed in the elastomer material of the condom, which band has reduced diameter relative to the diameter of the tubular portion 13. Band 23 is not coaxial with tubular portion 13, nor does band 23 form a transverse plane with the axis of tubular portion 13. Instead, band 23 can be seen to form a circumferential annular constriction that runs from the area where the scrotum 25 joins the underside of the penis 15, and circumferentially continues along both lateral sides that the scrotum joins the penis, up to the area where the abdominal wall 11 joins the penis, thereby overall forming a band that in side view is at a substantially greater angle than a prior art constriction band that is essentially transverse to the axis of the tubular portion of the condom. This difference is further illustrated in FIGS. 2 and 3, which compare and contrast the difference in the angles of the constriction bands between the invention and the prior art. In the prior art, constriction band 22 is virtually transverse to the axis of the condom, forming an area 24 that will bunch up when the condom is pulled on by the user, since such an area does not exist ergonomically in the male external genitalia during sexual activity.

Scrotal pouch 27 is seen to cover scrotum 25. Scrotal pouch 25 is continuous and integral with tubular portion 13, being connected by constriction band 23. Scrotal pouch 27 covers the scrotum over to the area of attachment of the scrotum to the junction of the genitocrural region and the anterior region of the perineum on the lateral and inferior sides of the penis, and to where the abdominal wall 11 joins the superior side of the penis, being secured by band 31. Band 31 is most preferably a toroidal band, being formed by the rolling up of a predetermined length of the elastomer material chosen for the condom. The toroidal ring enables a user to pull on the ring, which aids in putting on the condom.

In use, the condom of the invention is removed from its protective packaging, and pulled over the external genitalia, tucking the scrotum into the pouch and securely pulling the band 31 around the penis and scrotum as shown in FIG. 1. The condoms of the invention may e provided a several sizes such as small, medium and large.

As used herein, the term "elastomeric" in reference to thermoplastic materials useful for forming condom articles in accordance with the present invention means a material which subsequent to elongation thereof under an applied tensional force, regains at least a significant portion of its original dimensional characteristics when the applied tensional force is released. Suitable elastomeric materials for use in making condoms of the present invention include polyurethane materials, as for example the polyester-based polyurethane material commercially available from Mobay Corporation, Pittsburgh, Penn., under the trademark Texin®; polyester elastomers, such as the block copolymers of polybutylene terephthalate and long chain polyether glycol, which are available commercially from E.L Du Pont de Nemours and Company, Wilmington, Del. under the trademark Hytrel®; polyether block amides such as those commercially available from Atochem, Inc, Glennrock, N.J., under the trademark Pebax; multiblock rubber based copolymers, particularly those in which the rubber block component is based on butadiene, isoprene or thylene/butylene, such as the multiblock rubber based copolymers commercially available from Shell Chemical Company, Houston, Tex., under the trademark Kraton®; ethylene octene copolymers such as those commercially available from the Dow Chemical Company, Midland, Mich. under the trademark Attane®s; as well as any other suitable homopolymers and copolymers and mixtures thereof.

Polyester based polyurethanes, and multiblock rubber-based copolymers are most particularly preferred.

The composition of multiblock rubber based copolymers employed as materials of construction for the condom articles of the present invention may be varied widely, it being understood that the non rubber repeating units of the copolymer may be derived from any suitable monomers, as for example, methacrylate esters, such as methyl methacrylate, cyclohexylmethacrylate, vinyl arylenes, such as styrene, and so forth.

The most preferred multiblock rubber-based copolymers are those having an A-B-A structure comprising polystyrene endblocks and an elastomeric midblock In general, the non-rubber blocks in the multiblock rubber-based copolymer preferably are derived from monomers which are none-elastomeric in character, so that "soft" rubber blocks and "hard" none-elastomeric blocks are provided in the multiblock copolymer. Such hard blocks may suitably be derived from monomers having a glass transition temperature ($T_g$) of at least about 50° C., with styrene being generally preferred. The rubber block of such multiblock copolymers may be formed of repeating units derived from synthetic rubbers such as butadiene, isoprene, ethylene/butylene, etc., with butadiene and ethylene/butylene elastomeric blocks generally being preferred.

In the general use of a multiblock rubber based copolymer as the material of construction for the condom article of the present invention, the copolymer material preferably is characterized by the following physical properties: a Shore A hardness of from about 25 to about 100; a tensile strength of from about 500 to about 4500: a 300% modulus of from about 120 to about 1,000 psi; and an ultimate elongation of from about 200 to about 1400%.

With reference to the use of polyurethanes as materials of construction for the condom of the present invention, preferred material characteristics include: a specific gravity of from about 1.1 to about 1.25, a Shore A hardness from about 80 to about 95, a break tensile stress from about 4500 to about 6,000 psi; a tensile stress at 50% elongation of from about 720 to about 2400 psi, an ultimate elongation of from about 450% to about 600%, a flexural modulus of from about 4,000 to about 37,000 psi, and a tear strength of from about 500 to about 1,000 psi.

A condom of the present invention can be manufactured by several non-limiting processes. As a first example, U.S. Pat. No. 4,576,156, issued Mar. 18, 1986 to Namfred F. Dyke discloses a condom formed of a thermoplastic polyurethane material, having a generally cylindrical configuration with an open proximal end and a closed distal end. That condom has a thickness of from about 0.001 millimeters, or less, to about 0.25 millimeters. The thermoplastic polyurethane employed to form the condom is disclosed as having an average Shore A hardness of from about 50 to about 90, a tensile stress at 10% of elongation, between about 300 and 1,000 psi, and a tensile stress, at 300% elongation, between about 800 and 3,000 psi. Suitable thermoplastic polyurethane compounds for manufacturing the condom include polyether or polyester based urethane elastomers. A film of the polyurethane material in a 6 inch square is heated to a temperature high enough to soften the polymer but low enough to avoid chemical degradation, preferably in a clamping frame, and at a temperature of about 400 to 500 degrees Fahrenheit. The heated film then is brought into contact with a preformed mandril to cause the film to assume the shape of the mandril, preferably with application of a vacuum to the system in order to bring about uniformity in wall thickness. Thus, for example, an extruded film of Pellethane® X5036-80AA polyurethane (the Upjohn Company, Kalamazoo, Mich.) is clamped on a clamping frame and heated at 460 degrees Fahrenheit for 180 to 200 seconds, following which vacuum is drawn on the film and the mandril moved downward into the film. Vacuum is shut off as the mandril moves into the film, then is applied at the base of the mandril after it has moved down into the film completely, such vacuum causing the film to pull down tightly and assume the shape of the mandril. After 30 to 100 seconds of vacuum forming in this manner, the vacuum is released, excess material at the base is cut off, and the film is pulled off the mandril and then is dusted with powder As another example, European patent application 0 147 072 published Jul. 3, 1985, discloses a process for making a polyurethane condom with a uniform thickness of from about 1.5 to about 4 mils. A heat cured polyurethane prepolymer solvent solution is employed into which a mold is dipped and withdrawn for heat curing on the mold, The polyurethane prepolymer which is employed in the dipping medium is a prepolymer which is the reaction product of a polyisocyanate with at least one long chain polyol. The condom mold may be dipped into and withdrawn from the polyurethane solution at a rate of about 16 to about 90 centimeters per minute. The dwell time of the condom form in the polyurethane prepolymer solution is on the order of from about 20 to about 70 seconds. After withdrawal of the dipped mold, the polyurethane film deposited on the dipped form is air dried and then cured at elevated temperature of about 130 to 175 degrees Centigrade for about 20 to about 40 minutes. The polyol is amorphous at room temperature, has an average molecular weight of from about 500 to about 5,000, a hydroxy number of from 25 to about 22.4, and a NCO/OH ratio of from about 0.95:1 to 1.1:1.

Those of ordinary skill in the art of molded elastomeric condom manufacturing will readily be able to apply any of these methods or variations thereof to the manufacture of the condom of the invention, once the mandril, form or mold necessary to achieve the desired ergonomic shape has been fabricated.

While the invention has been described with reference to particular examples and embodiments, it will be apparent that numerous variations, alternatives, and modifications are possible, and accordingly all such variations, alternatives, and modifications are to be regarded as being within the spirit and scope of the present invention.

What is claimed is:

1. An elastomeric condom, comprising
   (a) a closed distal end portion to cover the glans of the penis;
   (b) a hollow tubular portion to cover the shaft of the penis, integrally continuous from said closed distal portion, having an inner surface and an outer surface, and having an open proximal end,
   (c) a scrotal pouch to cover the scrotum that is non-axial with said tubular portion, integrally continuous with said hollow tubular portion by an annular constricted band portion that is of lesser diameter than said tubular portion, said constricted band portion joining said tubular portion to said scrotal pouch at a non-perpendicular angle relative to the median axis of said tubular portion; and
   (d) a formed constricted band portion that terminates said scrotal pouch and that is non-axial with said tubular portion, the band being of lesser diameter than said scrotal pouch.

2. The condom as claimed in claim 1, wherein said distal end terminates in a teat of pre-determined volume for the collection and retention of ejaculated semen.

3. The condom as claimed in claim 1, wherein said annular constricted band that joins said tubular portion to said scrotal pouch comprises a ring of constricted elastomeric material that, when said condom is in place on the male genitalia, circumferentially covers the area that the scrotum is joined to the underside of the penis, the lateral areas that the scrotum is joined to the penis, and the area that the abdominal wall superiorly joins the penis.

4. The condom as claimed in claim 1, wherein said constricted band terminating said scrotal pouch comprises a toroidal ring of said elastomer.

5. An elastomeric condom, comprising
   (a) a closed distal end portion to cover the glans of the penis, said closed end portion terminating in a teat of predetermined volume for the collection of semen;
   (b) a non-axial hollow tubular portion to cover the shaft of the penis, integrally continuous from said closed distal portion, having an inner surface and an outer surface, and having an open proximal end,
   (c) a scrotal pouch to cover the scrotum that is non-axial with said tubular portion, integrally continuous with said hollow tubular portion by an annular constricted band portion that is of lesser diameter than said tubular portion, said constricted band portion joining said tubular portion to said scrotal pouch at a non-perpendicular angle relative to the median axis of said tubular portion; and
   (d) a formed constricted band portion that terminates said scrotal pouch and that is non-axial with said tubular portion, the band being of lesser diameter than said scrotal pouch.

6. An elastomeric condom, comprising
   (a) a closed distal end portion to cover the glans of the penis, said closed end portion terminating in a teat of predetermined volume for the collection of semen;
   (b) a non-axial hollow tubular portion to cover the shaft of the penis, integrally continuous from said closed distal portion, having an inner surface and an outer surface, and having an open proximal end, and having a lengthwise channel to conform to the shape of the corpus spongiosum of the erect penis;
   (c) a scrotal pouch to cover the scrotum that is non-axial with said tubular portion, integrally continuous with said hollow tubular portion by an annular constricted band portion that is of lesser diameter than said tubular portion, said constricted band portion joining said tubular portion to said scrotal pouch at a non-perpendicular angle relative to the median axis of said tubular portion; and
   (d) a formed constricted band portion that terminates said scrotal pouch and that is non-axial with said tubular portion, the band being of lesser diameter than said scrotal pouch, which band defines an annular ring over the portion of anatomy joining the abdominal wall and the anal perineum to the penis and scrotum.

* * * * *